US011298465B2

(12) United States Patent
Carlsson et al.

(10) Patent No.: US 11,298,465 B2
(45) Date of Patent: Apr. 12, 2022

(54) COMMUNICATION DEVICE FOR TRANSMITTING INFORMATION FROM A MEDICAMENT DELIVERY DEVICE

(71) Applicant: Carebay Europe Ltd., Sliema (SE)

(72) Inventors: Daniel Carlsson, Enskede (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 882 days.

(21) Appl. No.: 16/060,850

(22) PCT Filed: Nov. 3, 2016

(86) PCT No.: PCT/EP2016/076614
§ 371 (c)(1),
(2) Date: Jun. 8, 2018

(87) PCT Pub. No.: WO2017/097507
PCT Pub. Date: Jun. 15, 2017

(65) Prior Publication Data
US 2018/0369488 A1    Dec. 27, 2018

(30) Foreign Application Priority Data

Dec. 9, 2015  (EP) .................................... 15198783

(51) Int. Cl.
*A61M 5/315*    (2006.01)
*A61M 5/20*    (2006.01)
(Continued)

(52) U.S. Cl.
CPC ........ *A61M 5/3157* (2013.01); *A61M 5/2033* (2013.01); *A61M 5/24* (2013.01);
(Continued)

(58) Field of Classification Search
CPC ............ A61M 5/31583; A61M 5/3157; A61M 5/2033; A61M 5/24; A61M 5/31525
See application file for complete search history.

(56) References Cited

U.S. PATENT DOCUMENTS

| 2007/0021715 A1 | 1/2007 | Kohlbrenner et al. |
| 2008/0188813 A1* | 8/2008 | Miller .................... G01D 21/00 604/207 |

(Continued)

FOREIGN PATENT DOCUMENTS

| EP | 0749332 B1 | 5/2005 |
| WO | 2006045525 A1 | 5/2006 |

(Continued)

OTHER PUBLICATIONS

Search Report issued in Taiwanese Patent Application No. 105137110 dated Jan. 10, 2018.

*Primary Examiner* — Scott J Medway
*Assistant Examiner* — John A Doubrava
(74) *Attorney, Agent, or Firm* — McDonnell Boehnen Hulbert & Berghoff LLP

(57) ABSTRACT

A communication device arranged for transmitting information from a medicament delivery device is presented. The communication device includes at least one rotation detection arrangement, the at least one rotation detection arrangement being configured to detect a rotation of at least one physical part of the medicament delivery device. The communication device also includes at least one determination unit configured to determine information related to a medicament delivery performed by the medicament delivery device. The communication device further includes at least one activation unit configured to activate the at least one determination unit based on the detected rotation. Also, the communication device includes at least one transmission
(Continued)

unit configured to provide a wireless transmission of the information to an external receiving device.

11 Claims, 16 Drawing Sheets

(51) Int. Cl.
    *A61M 5/24* (2006.01)
    *A61M 5/31* (2006.01)
    *A61M 5/32* (2006.01)
    *G16H 20/17* (2018.01)

(52) U.S. Cl.
    CPC ..... *A61M 5/31525* (2013.01); *A61M 5/31583* (2013.01); *A61M 5/3204* (2013.01); *A61M 5/326* (2013.01); *A61M 2005/206* (2013.01); *A61M 2005/2013* (2013.01); *A61M 2005/3125* (2013.01); *A61M 2205/3334* (2013.01); *A61M 2205/3375* (2013.01); *A61M 2205/3561* (2013.01); *A61M 2205/502* (2013.01); *A61M 2205/581* (2013.01); *A61M 2205/582* (2013.01); *A61M 2205/6009* (2013.01); *A61M 2205/6027* (2013.01); *A61M 2205/6063* (2013.01); *G16H 20/17* (2018.01)

(56) References Cited

U.S. PATENT DOCUMENTS

| | | | |
|---|---|---|---|
| 2015/0202375 A1* | 7/2015 | Schabbach | A61M 5/24 604/207 |
| 2016/0030680 A1* | 2/2016 | Veasey | A61M 5/31568 604/211 |
| 2016/0367763 A1 | 12/2016 | Tschirren et al. | |

FOREIGN PATENT DOCUMENTS

| | | |
|---|---|---|
| WO | 2012127046 A2 | 11/2012 |
| WO | 2014037331 A1 | 3/2014 |
| WO | 2015131294 A1 | 9/2015 |

* cited by examiner

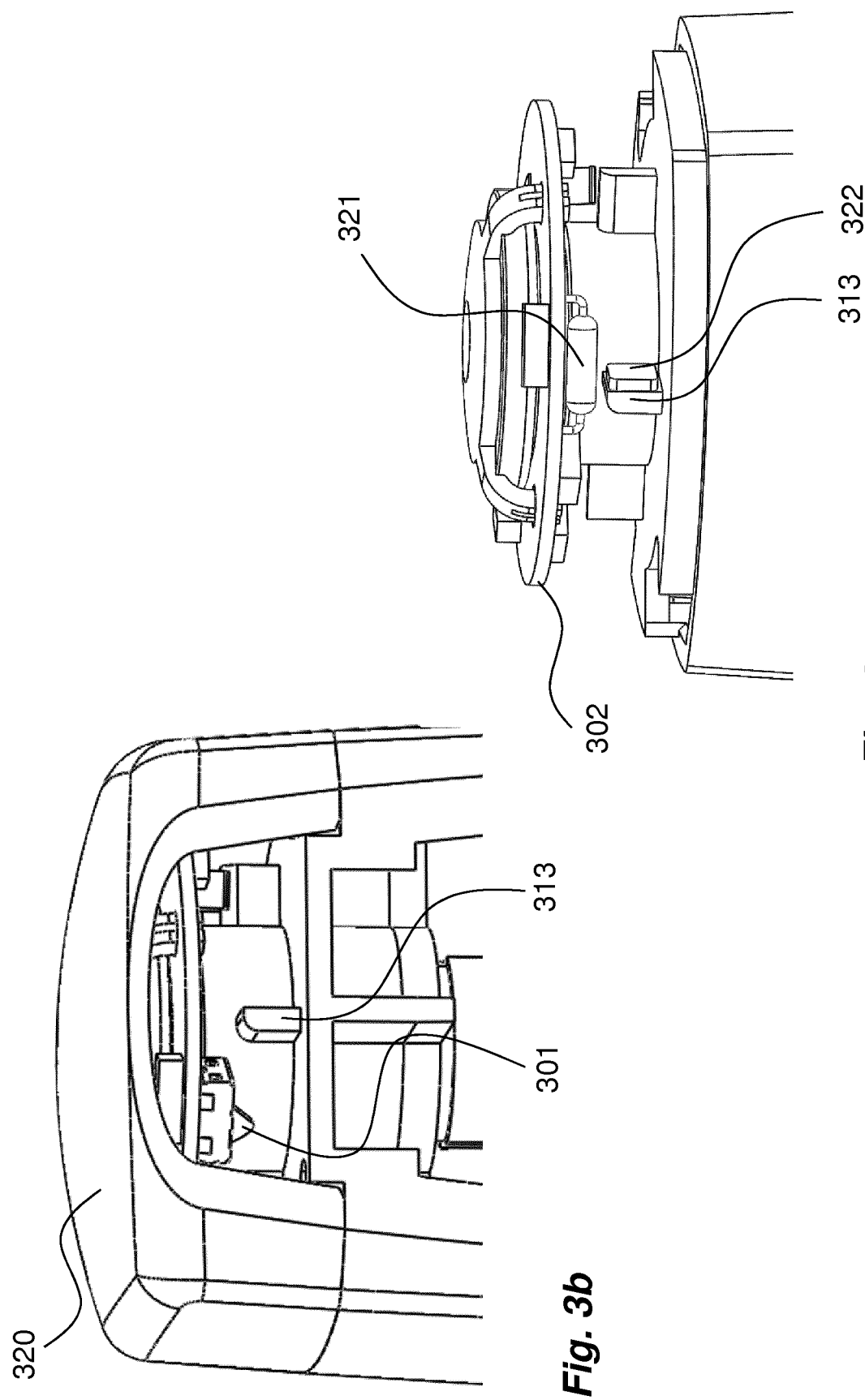

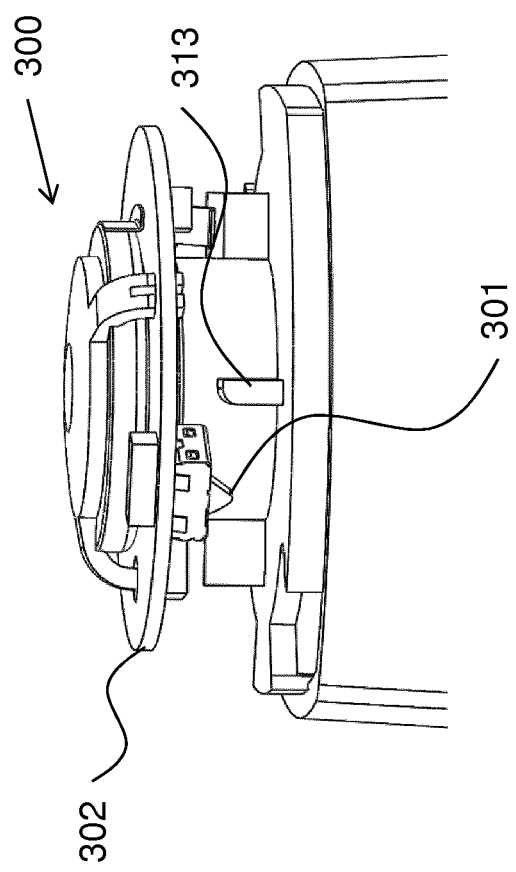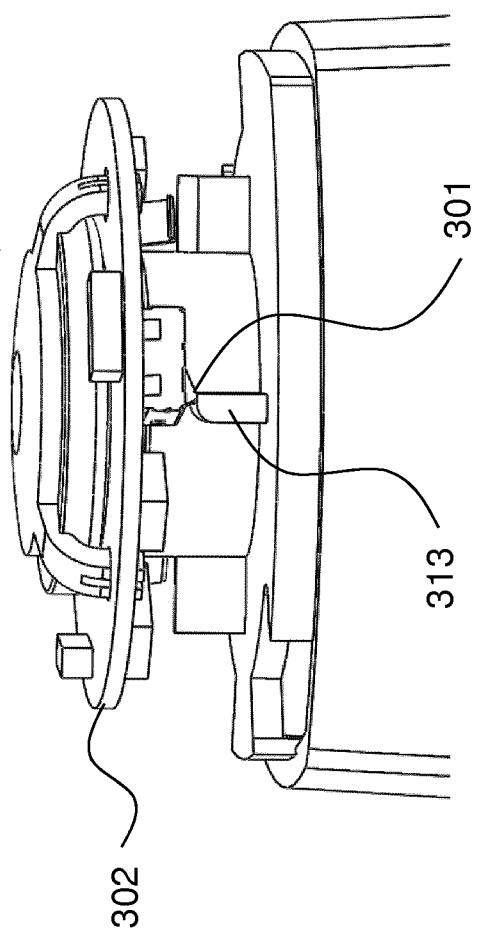
Fig. 4a
Fig. 4b

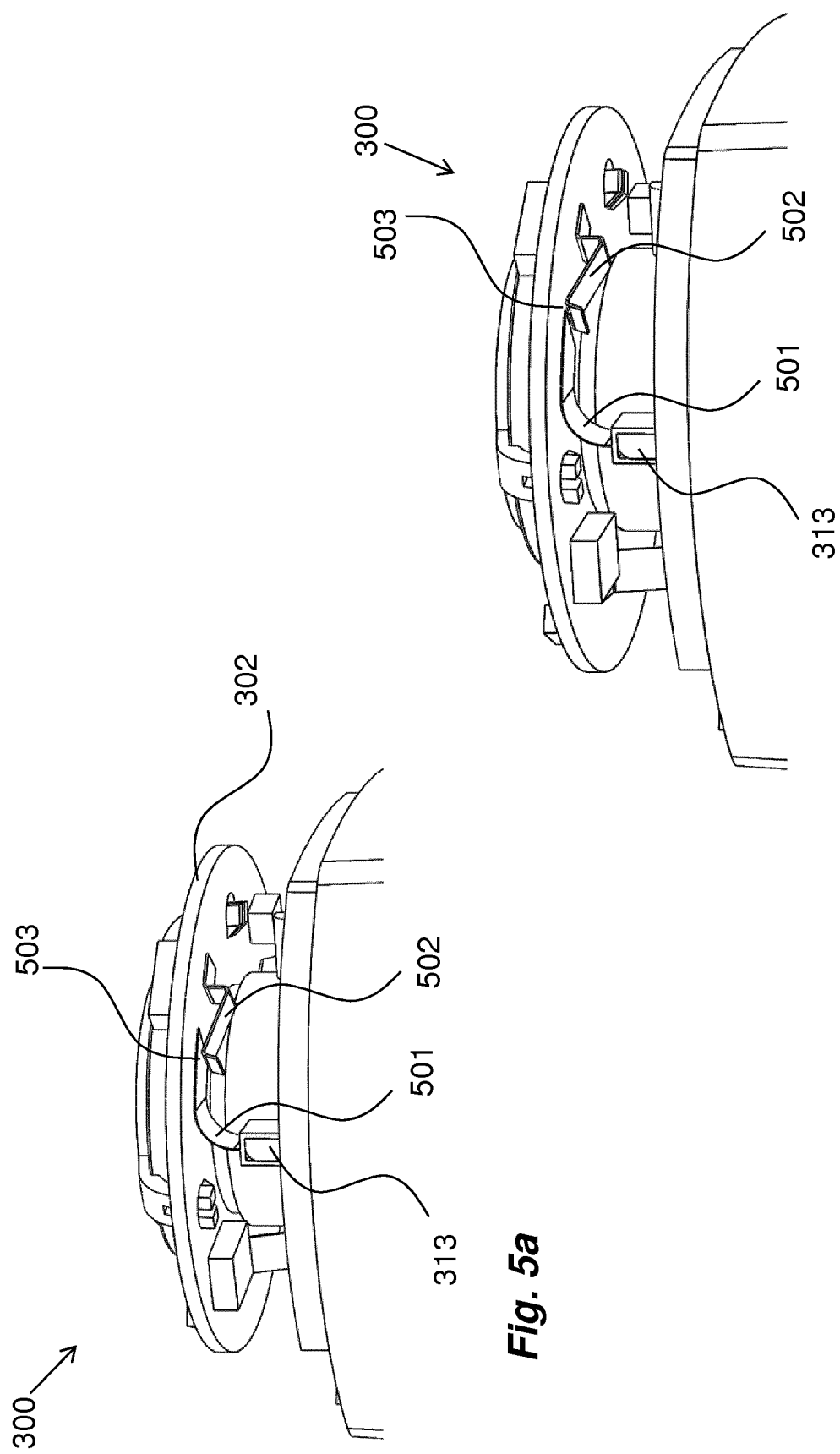

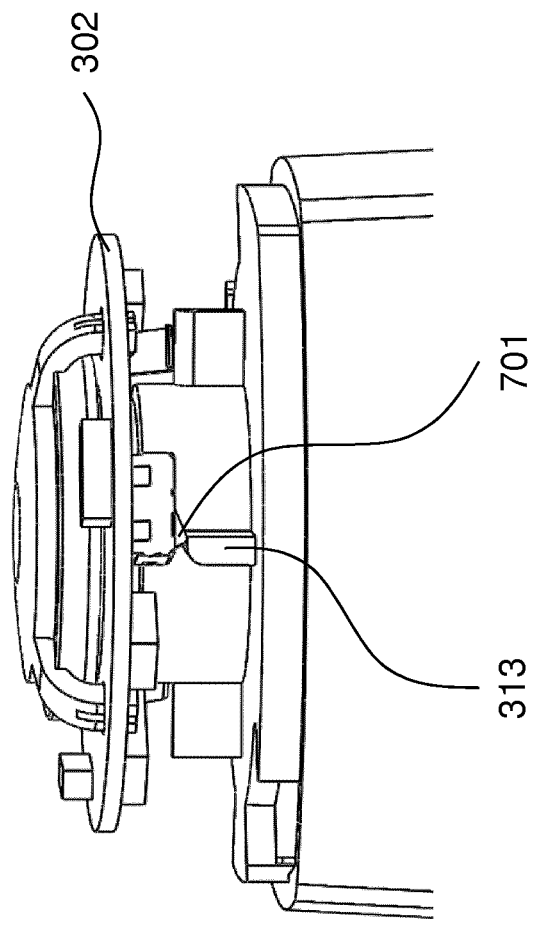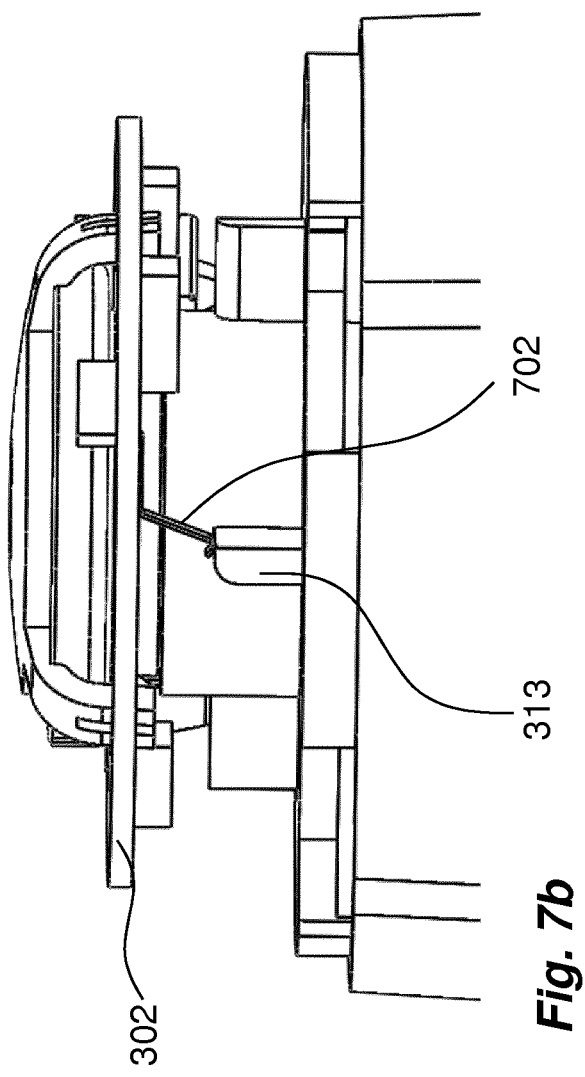

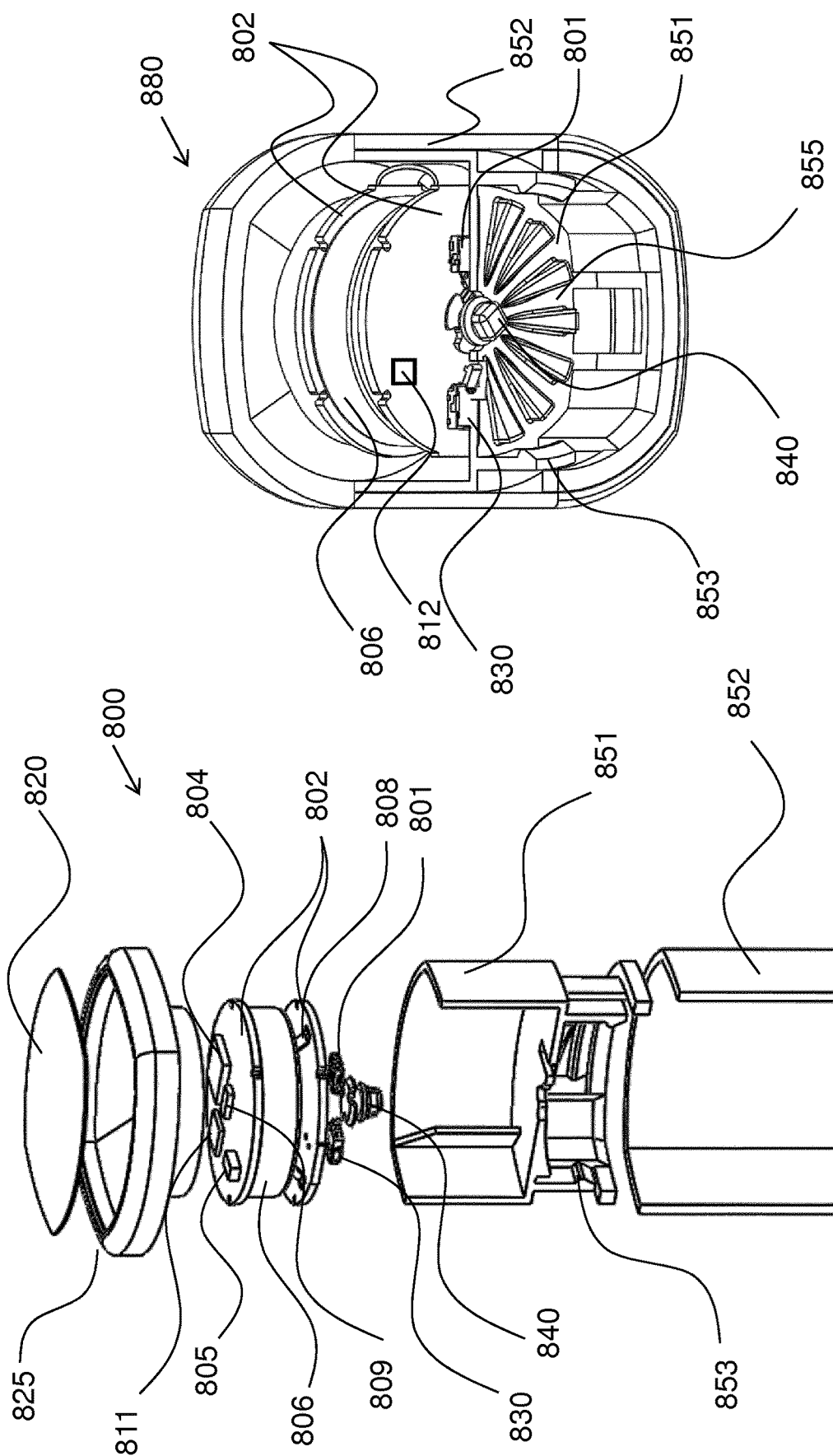

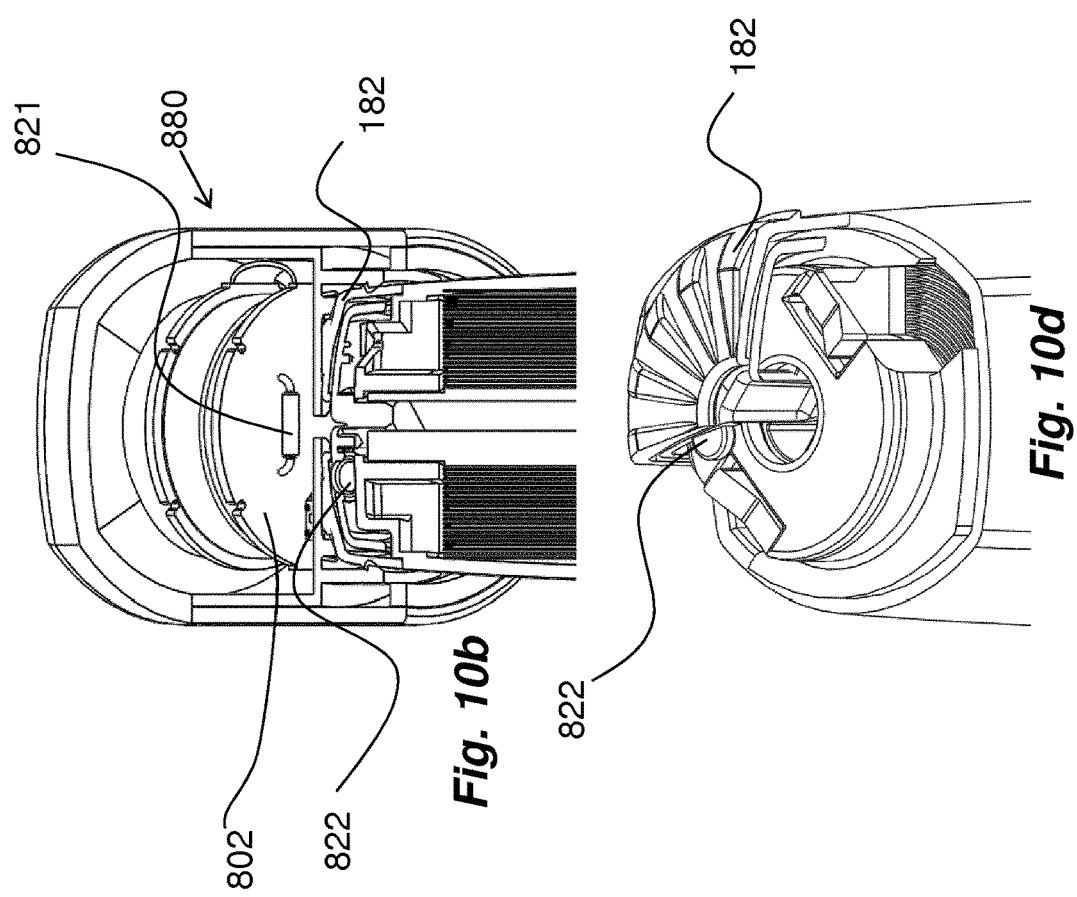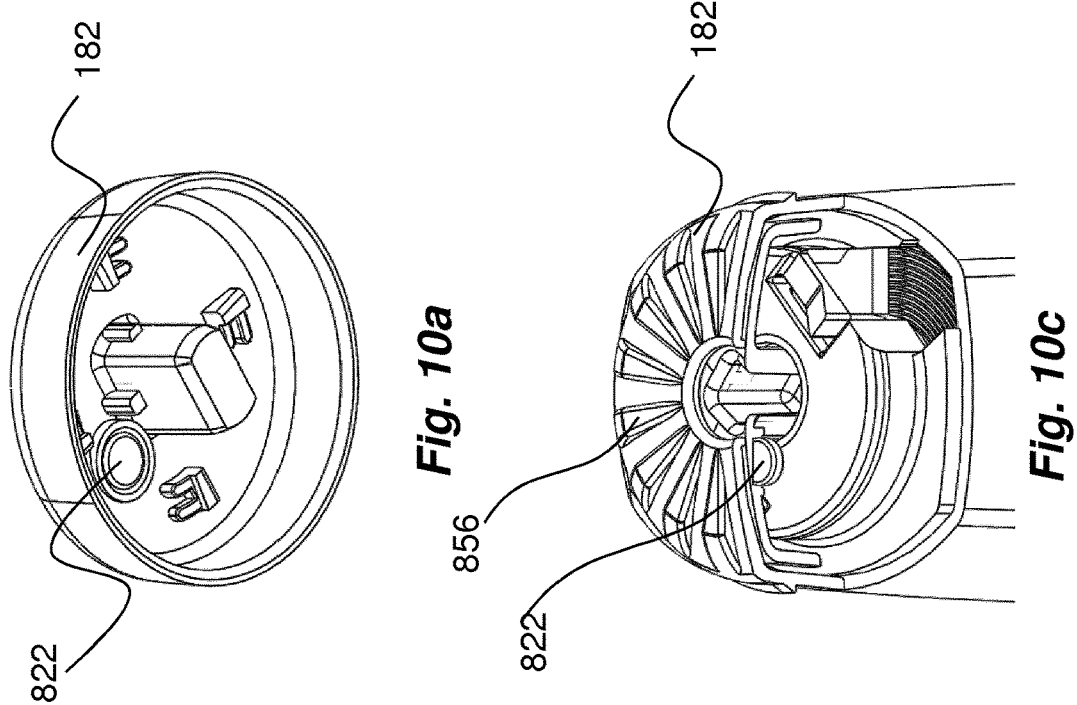

COMMUNICATION DEVICE FOR TRANSMITTING INFORMATION FROM A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/076614 filed Nov. 3, 2016, which claims priority to European Patent Application No. 15198783.1 filed Dec. 9, 2015. The entire disclosure contents of these applications are hereby incorporated by reference into the present application.

FIELD OF INVENTION

The present invention relates to a communication device as defined in the preamble of claim 1.

BACKGROUND OF INVENTION

The following background information is a description of the background of the present invention, which thus not necessarily has to be a description of prior art.

Medicament delivery devices, such as for example injection devices, auto-injection devices or pen-injection devices, are nowadays commonly used for helping patients to take their medicaments/drugs. Other kind of medicament delivery devices may be inhalers, eye dispensers, or gel dispensers. Such medicament delivery devices may have one or more automatic functions providing/facilitating the delivery of the medicaments, such as for example automatic penetration, automatic injection and/or automatic safety means for preventing from accidental needle sticks.

The medicament delivery devices can e.g. be activated by pressing the device against a body part. The device can then be pressed against the body part for example by the patient and/or by trained personnel, such as physicians or nurses. The medicament delivery devices often comprise a housing, a power source as e.g. a spirally wound compression spring acting on a plunger rod which in its turn acts on a stopper inside a medicament container for expelling the medicament through a needle attached to the container when being pressed against the body part. Hereby, an automatic or semiautomatic delivery of the medicament is provided by the device.

Medicament delivery devices help patients taking their medicaments. Especially, the right dosage of the medicament is secured by use of the device itself, since the amount of medicament/drug in the medicament container can be set/chosen to correspond to the prescribed dose. Normally, the medicament delivery device is essentially completely emptied by the delivery, whereby the prescribed dose of medicament is injected to the patient.

However, the adherence/compliance to take the medicaments according to a prescribed scheme over time is poor for some patients and/or patient groups. There can be many reasons for such non-compliance. One reason can be that the patient is in pain and/or that the delivery of the medicament itself is unpleasant, or maybe even painful. Another reason can be that the patient simply forgets to take the medicament. It should be noted that some sicknesses/diseases/conditions and/or medicaments affect the ability to remember things, and therefore increase the risk for the patient to forget taking the medication.

When the patient does not follow the prescribed medication scheme, there is a risk that the sickness/disease/condition is prolonged or worsened, and/or that the patient is stricken with further complications. A prolonged or worsened sickness/disease/condition and/or further complications of course adds both to the suffering of the patient and to the total costs for the medicaments and medical care. Therefore, medical care personal treating the patient, as well as authorities and/or insurance companies paying for the treatment, want to be able to monitor the intake of medicaments for the patient.

Today, the intake of the medicaments can be estimated based on a count of how many of the prescriptions having been made up for a patient that are actually collected by the patient at e.g. a pharmacy. This is, however, a very uncertain method, since it is not at all guaranteed that a collected medicament is also taken by the patient.

The intake of medicaments can today also be monitored by the use of applications/computer programs, in which the patient can enter data after each time a medicament dose has been taken. However, the probability that patients being likely not to take the medicament would remember and/or go through the extra work to enter data into such applications/computer programs is low. Thus, the information gathered by such applications/computer programs is very unreliable. Also, it is not at all certain that a missed entry in the application/computer program means that the medicament has not been taken. It is also not guaranteed that an entry in the application/computer program means that the medicine was taken.

SUMMARY OF INVENTION

It is therefore an object to solve at least some of the above mentioned disadvantages and to provide a device which facilitates reliable monitoring of that patients follow their prescribed medication scheme, i.e. that the patients take the prescribed dose at the prescribed time instants.

The object is achieved by the above mentioned communication device according to the characterizing portion of claim 1.

According to an aspect of the present invention, a communication device arranged for transmitting information from a medicament delivery device is presented.

The communication device includes at least one rotation detection arrangement, the at least one rotation detection arrangement being configured to detect a rotation of at least one physical part of the medicament delivery device.

The communication device also includes at least one determination unit configured to determine information related to a medicament delivery performed by the medicament delivery device.

The communication device further includes at least one activation unit configured to activate the at least one determination unit based on the detected rotation.

Also, the communication device includes at least one transmission unit configured to provide a wireless transmission of the information to an external receiving device.

By usage of the present invention, the suffering of the patients can be minimized. Also, the overall cost for medical care can be lowered for some patients and/or patient groups.

The present invention provides for automated and reliable monitoring of whether patients follow their prescribed medication schemes or not. Based on this monitoring, e.g. a doctor treating a patient can directly contact a patient not following the medication scheme to hear what the problem is. Thus, the monitoring could help a doctor to find out which of his patients that need additional information and/or help with taking the medicaments. Maybe, the doctor could also come to the conclusion that a change of medicament should be made in order to increase the compliance of the patient, e.g. if the prescribed medicament is unpleasant/uncomfortable for the patient to take.

Also, authorities and/or insurance companies paying for the medical care can, based on the monitoring, contact the patient to inform the patient that they will stop paying for the treatment if the patient does not follow the prescribed medication scheme. An insurance company could also use the monitoring for adjusting the pricing level of a health care insurance for the patient.

The present invention can thus be used for improving the compliance to a prescribed medication scheme, which lowers the risk for a prolonged sickness/disease/condition and/or lowers the risk that the patient is stricken with further complications. Hereby, the suffering for the patient is minimized, and the total costs for the medicaments and medical care are also lowered.

According to an embodiment of the present invention, the at least one rotation detection arrangement includes at least one mechanical switch configured to be compressed by the rotation.

According to an embodiment of the present invention, the at least one mechanical switch may be configured such that the mechanical switch is rotated by the rotation, and is arranged in relation to at least one fixed activation wall of the medicament delivery device such that the mechanical switch is pressed against the at least one activation wall by the rotation. As an alternative, the mechanical switch may be fixed, and is arranged in relation a rotator of the communication device, the rotator being rotated by the rotation such that the rotator is pressed against the mechanical switch by the rotation.

According to an embodiment of the present invention, the at least one rotation detection arrangement may include at least one electromagnetic switch configured to be activated by the rotation.

According to an embodiment of the present invention, the at least one electromagnetic switch may be configured such that the at least one electromagnetic switch is rotated by the rotation, and is arranged in relation to at least one magnet being fixed on the medicament delivery device such that the at least one electromagnetic switch is activated when the at least one electromagnetic switch is brought adjacent to the magnet by the rotation. As an alternative, the at least one electromagnetic switch may be fixed and is arranged in relation to at least one magnet being configured to be rotated by the rotation such that the at least one electromagnetic switch is activated when the at least one magnet is brought adjacent to the at least one electromagnetic switch by the rotation.

According to an embodiment of the present invention, the at least one rotation detection arrangement may include at least one insulating strip being positioned between two contact points before the rotation, the at least one insulating strip being configured to be removed from the two contact points by the rotation.

According to an embodiment of the present invention, the at least one insulating strip may be attached to a fixed part of the medicament delivery device, and the two contact points are configured to be rotated by the rotation, such that a short circuit is created between the two contact points when the at least one insulating strip is removed from between the two contact points by the rotation.

According to an embodiment of the present invention, the at least one rotation detection arrangement may include at least one vibration sensor configured to pick up a predetermined vibration profile corresponding to a vibration profile being created by the medicament delivery device by the rotation.

According to an embodiment of the present invention, the at least one determination unit may be configured to determine information based on a number of revolutions of the at least one rotating physical part, the number of revolutions being measured by the at least one rotation detection arrangement.

According to an embodiment of the present invention, the at least one determination unit may be configured to determine the information based on preconfigured data and/or measured data related to the medicament delivery, the data including one or more in the group of:
- an identification number for the medicament delivery device;
- an identification number for a medicament being delivered by the medicament delivery device;
- an identification number for a patient using the medicament delivery device; and
- an elapsed time since a delivery of a medicament occurred.

According to an embodiment of the present invention, the communication device further may include at least one indication unit configured to provide at least one indication of that the medicament delivery is performed, the at least one indication being provided during the delivery and also during a predetermined time period after the delivery has ended.

According to an embodiment of the present invention, the communication device may further include at least one indication unit including one or more in the group of:
- at least one light source configured to emit light as the at least one indication;
- at least one light guide configured to guide light being emitted by at least one light source as the at least one indication;
- at least one mechanical audible indication source configured to be compressed and released by the rotation, thereby emitting the audible indication; and
- at least one mechanical tactile indication source configured to be compressed and released by the rotation, thereby providing the tactile indication.

According to an embodiment of the present invention, the communication device may be included within a housing of the medicament delivery device.

According to an embodiment of the present invention, the communication device may be included in an external unit, the external unit being releasably attachable to the medicament delivery device.

According to an embodiment of the present invention, the communication device may include an attachment switch, the attachment switch being activated when the communication device is releasably attached to the medicament delivery device, thereby enabling activation of the communication device.

The above mentioned units and arrangements, such as the at least one rotation detection arrangement, the at least one activation unit, the at least one determination unit, the at least one transmission unit and/or the at least one indication unit, can be at least partly implemented in a computer program, which, when it is executed in a processor, instructs the processor to execute the steps taken by the units and arrangements, respectively. The computer program is often constituted by a computer program product stored on a non-transitory/non-volatile digital storage medium, in which the computer program is incorporated in the computer-readable medium of the computer program product. Said computer-readable medium comprises a suitable memory, such as, for example: ROM (Read-Only Memory), PROM (Programmable Read-Only Memory), EPROM (Erasable PROM), Flash memory, EEPROM (Electrically Erasable PROM), a hard disk unit, etc.

Here and in this document, the arrangements and/or units are often described as being arranged for performing steps according to the invention. This also includes that the units are designed to and/or configured to perform these steps. For example, these arrangements and/or units can at least partly correspond to groups of instructions, which can be in the form of programming code, that are input into, and are utilized by the processor when the units and/or arrangements are active and/or are utilized for performing its step, respectively.

Detailed exemplary embodiments and advantages of the communication device according to the invention will now be described with reference to the appended drawings illustrating some preferred embodiments.

BRIEF DESCRIPTION OF THE DRAWINGS

Embodiments of the invention are described in more detail with reference to attached drawings illustrating examples of embodiments of the invention in which:

FIGS. 3a-b show a communication device according to some embodiments,

FIGS. 4a-c show parts of a communication device according to some embodiments,

FIGS. 5a-b show parts of a communication device according to some embodiments,

FIGS. 7a-c show parts of a communication device according to some embodiments,

FIGS. 8a-c show a communication device according to some embodiments,

FIGS. 10a-d show parts of a communication device according to some embodiments.

DETAILED DESCRIPTION OF INVENTION

In the following, the present invention is often exemplified as implemented in an injection device. The present invention can, however, be implemented in essentially all kinds of medicament delivery devices that include at least one physical part which rotates when the medicament is delivered to the patient, and is thus not restricted to implementation in injection devices.

Figure 1A:
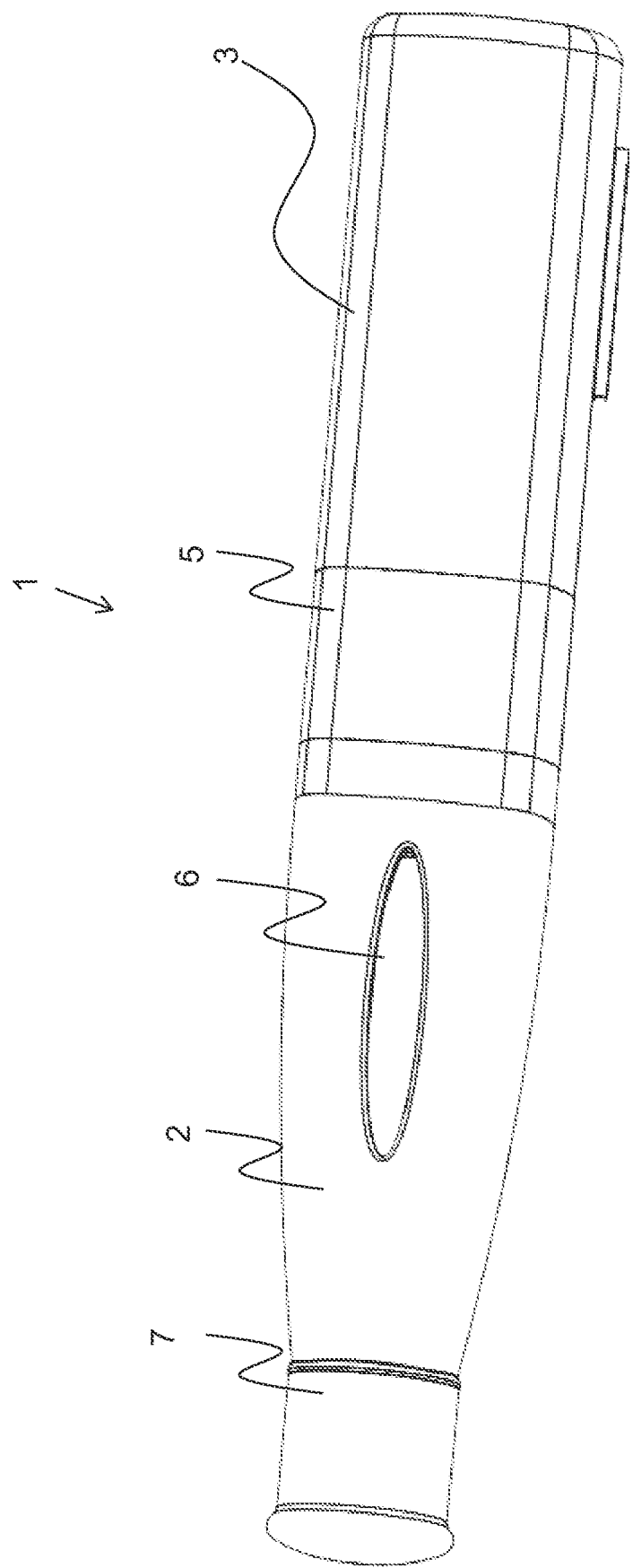
FIGS. 1a-c show a medicament delivery device.
Figure 1B:
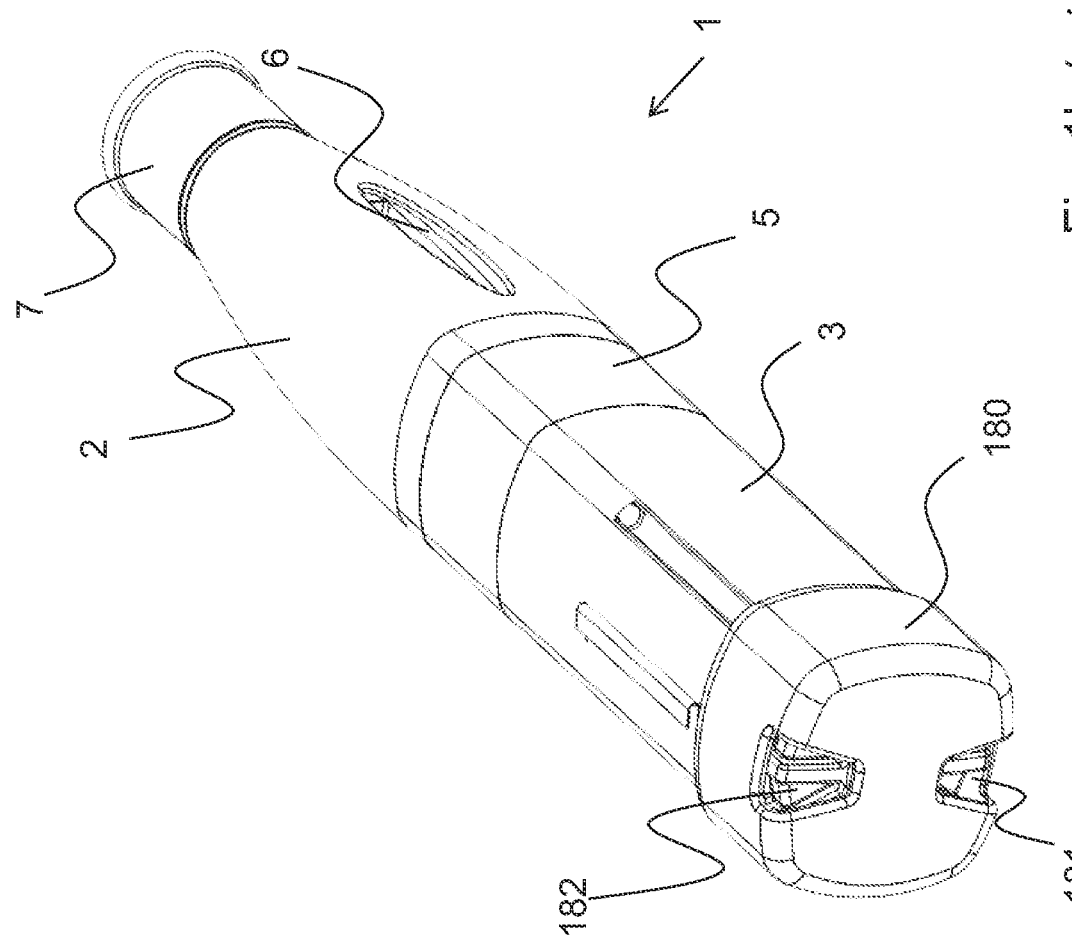
Figure 1C:
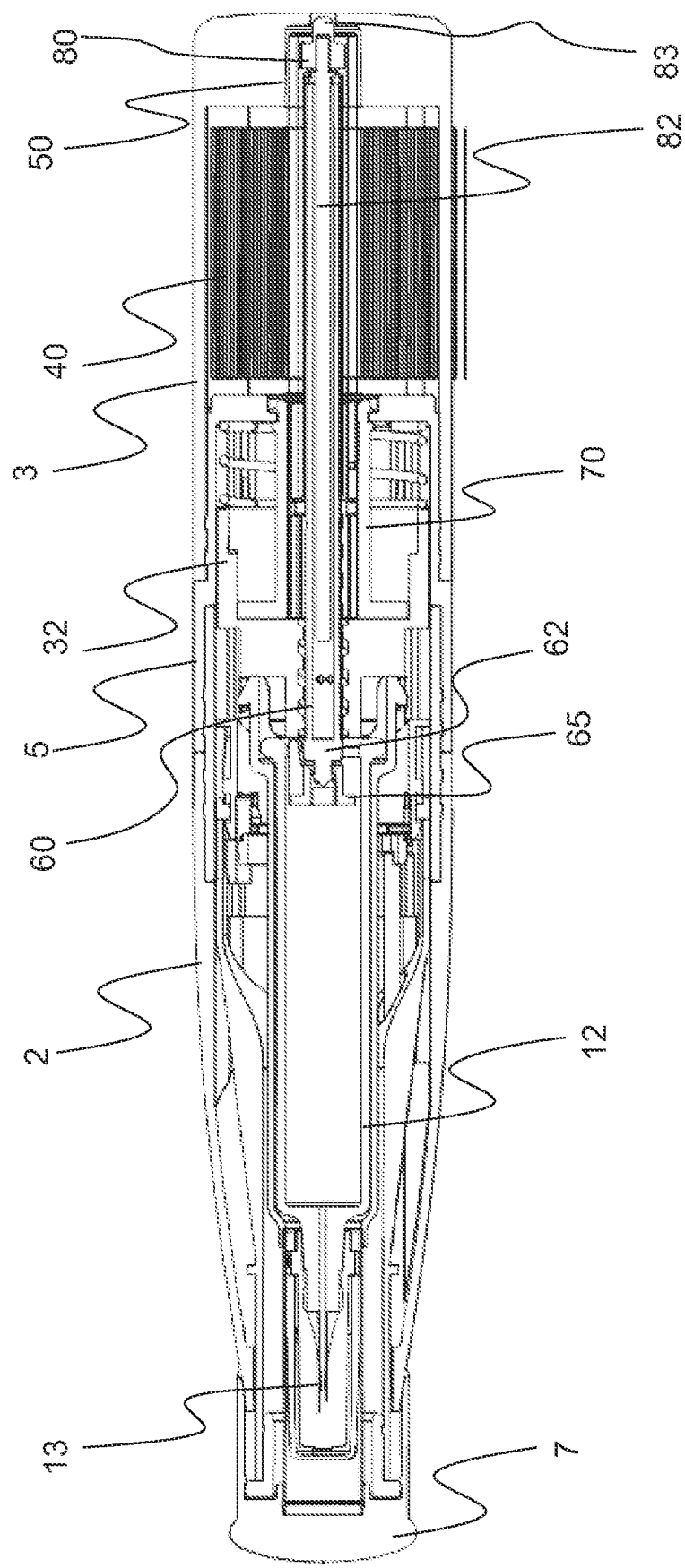

In FIGS. 1a-c, a non-limiting example of a medicament delivery device 1 is shown. In FIGS. 1a-c, the same components are labeled with identical reference numerals.

FIG. 1a shows a perspective view of a medicament delivery device 1, in which the communication device according to the present invention can be implemented. The medicament delivery device 1 has a housing that comprises a proximal housing part 2, a distal housing part 3, a proximal intermediate housing part (not shown in FIG. 1a), and a distal intermediate housing part 5. In the assembled state of the medicament delivery device 1, the proximal housing part 2, the distal housing part 3, and the distal intermediate housing part 5 form the outer surface or appearance of the medicament delivery device 1.

In this document, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

As shown in FIG. 1a, the proximal housing part 2 comprises at least one window 6, which allows the user to view the state of the injection, i.e. whether the medicament delivery device 1 is still in its initial stage with the medicament not yet being injected, or whether the medicament container is already emptied. Through window 6, the user can see the medicament container accommodated at least in the proximal housing part 2. FIG. 1a also shows a front cap 7, which closes the proximal opening of the proximal housing part 2 until the medicament delivery device 1 is used.

FIG. 1b shows a perspective view of the medicament delivery device 1 shown in FIG. 1a. As shown in FIG. 1b, the medicament delivery device 1 can include an indicator assembly 180. The indicator assembly comprises a cap having at least one opening 181. Through this opening 181, the user can see a signaling element in the form of a rotatable wheel or disk 182. The wheel or disk 182 is rotated when the medicament is delivered to the patient, thereby indicating that an injection is taking place. As is understood by a skilled person, the indicator assembly 180 can have a large number of forms and/or features.

FIG. 1c shows some, not all, internal parts of the medicament delivery device illustrated in FIGS. 1a-b. A medicament delivery device includes a large number of internal parts. In this document, however, only the parts of a medicament delivery device, exemplified by an injector, being essential for understanding the present invention are described. For a more complete description of the medicament delivery device parts, and their functions, reference is made to document US2014/0148763.

FIG. 1c shows a sectional view of the medicament delivery device 1 in its initial position, i.e. before the medicament has been delivered.

The medicament delivery device 1 includes a needle 13 of a medicament container 12 being covered by a rigid needle shield. A plunger driver 50 is initially, i.e. before delivery, rotationally locked to a plunger drive locking member 70, but is slidable in axial direction in relation to plunger drive locking member 70. The plunger rod 60 may comprise a threaded structure as well as at least one longitudinal groove. At the proximal end, the plunger rod 60 comprises a plunger rod tip 62 onto which a spinner element 65 can be attached by snap fit. The spinner element 65 acts on a stopper in the medicament container 12 in order to deliver the medicament.

In the initial stage of the medicament delivery device 1, i.e. prior to its use, a proximal part of the plunger rod 60 is received in the central opening of the container driver 32. However, once the plunger drive locking member 70 is free to rotate, which happens when the delivery starts, the plunger driver 50 and the plunger rod 60 also start to rotate, caused by a first spring 40.

A central opening of the container driver 32 comprises a threaded structure that engages with the threads of the plunger rod 60. Thus, the threaded proximal section of the plunger rod 60 is screw threaded in the interior of the container driver 32. Due to this threaded engagement, rotation of the plunger rod 60 upon use of the medicament delivery device results in an axial displacement of the plunger rod 60 towards the proximal end of the medicament delivery device. In other words, the plunger rod 60 is rotated by the thread engagement in the direction of the medicament container 12, and causes the stopper in the medicament container 12 and in abutment with spinner 65 to move towards the proximal end of the medicament container 12 in order to expel medicament through the injection needle 13.

When the plunger rod 60 is proximally advanced, during the delivery, the indicator 80 and the indicator rod 82, being part of the indicator assembly, are forced distally. The plunger rod 60 is then also rotationally locked to the plunger driver 50 but may axially slide along ribs of the plunger driver 50. The plunger driver 50 is connected to the inner end of the first spring 40, whereby a force applied to the plunger driver 50 by the first spring 40 is transmitted to the plunger rod 60. Thus, the plunger driver 50 is rotated by the first spring 40 when the medicament is expelled/injected.

The torque force of the first spring 40 will continue to drive the plunger rod 60 towards the proximal end of the medicament delivery device 1 pressing the stopper to expel medicament through the needle 13. The container driver 32 slides over along the plunger rod 60 as the plunger rod 60 continues to move towards the proximal end of the device. The delivery is completed when the stopper is at the proximal end of the medicament container 12.

When the plunger rod 60 is fully rotated towards the proximal end of medicament delivery device 1, a second spring (not shown) coaxially arranged with the indicator rod 82 causes the indicator assembly to move distally until the indicator 80 contacts the distal front surface of the distal housing part 3. This causes the distal protrusion of the indicator 80 to project through an indicator opening 83 provided in the centre of the distal wall of the distal housing part 3. This provides a visible and tactile indication to the user that the complete dose has been expelled.

In FIG. 1c, the relative arrangement of the indicator 80, the indicator rod 82, and the indicator distal opening 83 can be seen. The indicator rod 82 substantially extends within a central bore of the plunger rod 60. At the distal end of the medicament delivery device 1, a distal part of the indicator rod 82 extends beyond the distal end of the plunger rod 60, and is received in an inner central bore of the indicator 80.

As mentioned above, the communication device according to the present invention may be implemented in a large number of different medicament delivery devices. The medicament delivery device illustrated in FIGS. 1a-c is only one non-limiting example of such medicament delivery devices.

Figure 2B:
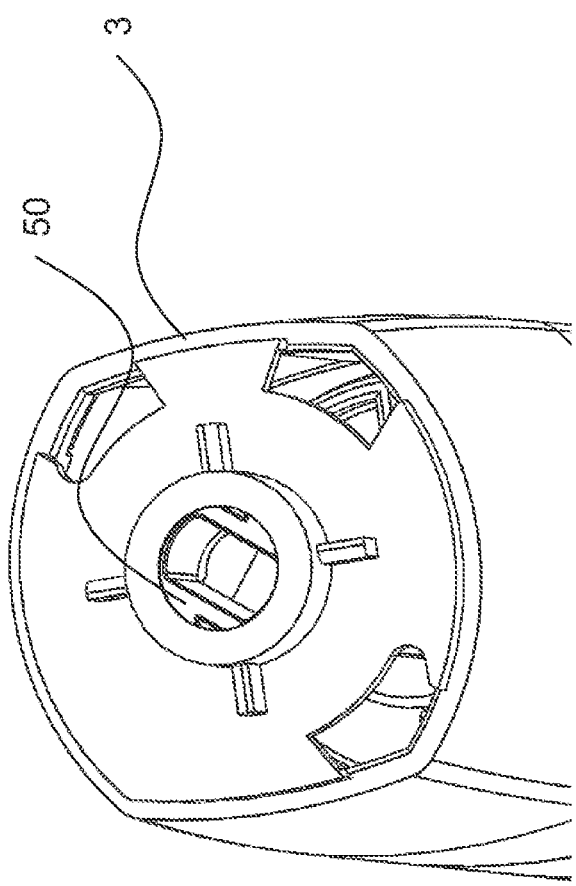
FIGS. 2a-b show details of a medicament delivery device.
Figure 2A:
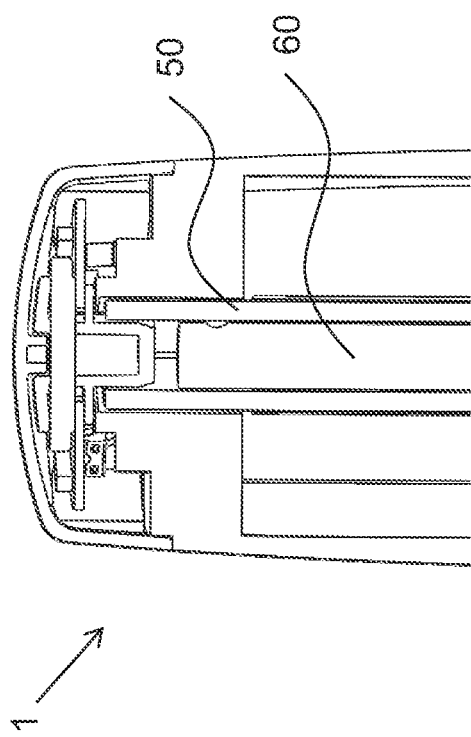

FIGS. 2a-b show a sectional view and a perspective view, respectively, of the distal part of a medicament delivery device 1, including the distal housing part 3, the plunger driver 50 and the plunger rod 60. As described above, when the medicament delivery device 1 is activated to expel medicament, the first spring 40 provides a force which rotates the plunger driver 50. The plunger driver 50 then rotates the plunger rod 60.

According to an aspect of the present invention, a communication device arranged for transmitting information from a medicament delivery device is presented.

The communication device includes at least one rotation detection arrangement, the at least one rotation detection arrangement being configured to detect a rotation of at least one physical part of the medicament delivery device. As is described above and below, a number of physical parts of the medicament delivery device, such as the plunger 60, the plunger driver 50 and/or the signaling element 182, are rotated when a medicament delivery is performed by the medicament delivery device. Thus, a detected rotation of one of these parts can be used as a clear indication of that a medicament delivery is taking place.

The communication device also includes at least one determination unit configured to determine information related to a medicament delivery performed by the medicament delivery device. The information can be based on preconfigured data and/or measured data related to the medicament delivery. Such data may include e.g. an identification number identifying the medicament delivery device, an identification number identifying a medicament/drug being delivered by the medicament delivery device, an identification number identifying a patient using the medicament delivery device, and/or an elapsed period of time since a delivery of a medicament/drug occurred.

The communication device further includes at least one activation unit configured to activate the at least one determination unit based on the detected rotation. Thus, the at least one determination unit will be activated when a medicament delivery is performed.

Also, the communication device includes at least one transmission unit configured to provide a wireless transmission of the information to an external receiving device. The transmission may be performed in essentially any format being suitable for transfer of data wirelessly, such as according to for example a Bluetooth transmission protocol or another similar short range transmission protocols, or according to a cellular communication protocol of some kind. The external receiving device can be essentially any device including a receiver, such as for example be a portable device, such as a tablet, a smartphone or a laptop, or a stationary device, such as a stationary computer, a server equipment, a router equipment or a network hub.

According to different embodiments of the present invention, the at least one activation unit is configured to activate the at least one determination unit and/or the at least one transmission unit based on the detected rotation. According to an embodiment, the whole communication device is activated by the at least one activation unit when a rotation is detected.

According to an embodiment of the present invention, the at least one rotation detection arrangement includes at least one mechanical switch 301 configured to be compressed, and subsequently released, by the rotation of the at least one physical part during the medicament delivery.

Figure 3A:
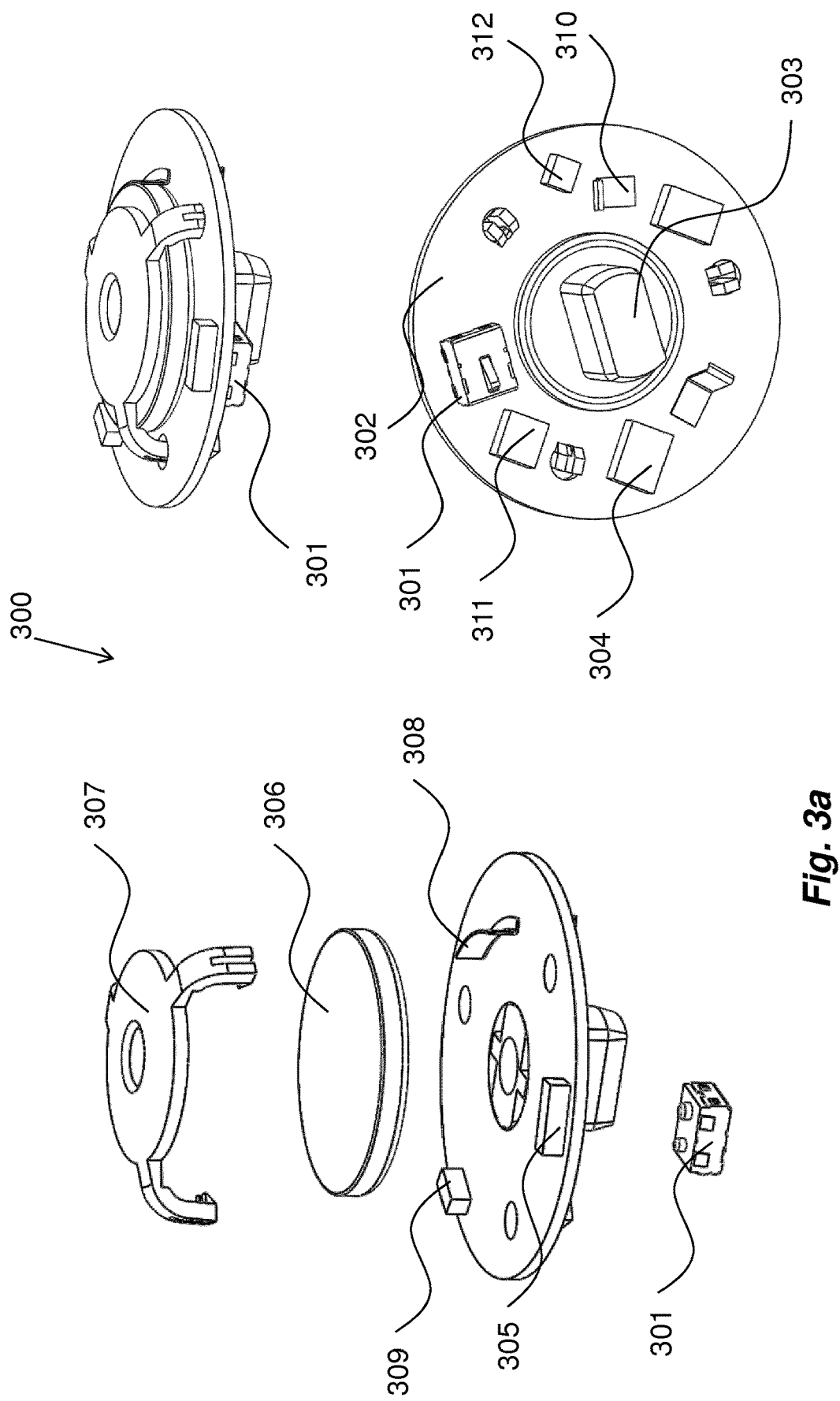

FIG. 3a shows an exploded view of a number of parts that can be included in a communication device 300 according to different embodiments of the present invention. According to an embodiment, the communication device 300 itself is configured to rotate with the rotation of the at least one physical parts 50, 60, 182, as is described below.

The communication device 300 illustrated in FIG. 3a includes a rotatable Printed Circuit Board (PCB) 302 being connected to the one or more rotating physical parts 50, 60, 182 by a driver/shaft 303. A transmission unit 304, such as e.g. a Bluetooth transmission unit, and an antenna unit 305 are arranged on the PCB 302 in order to transmit the information to the external receiver. The electronic circuits of the communication device 300 are provided with electrical power by a battery 306, being held by a battery holder/bearing hub 307, via a battery connector 308. The communication device 300 can also, according to some embodiments, include at least one light source 309, such as a Light Emitting Diode (LED), at least one vibration generator 310, such as at least one click-sound generator, at least one vibration sensor 312, such as at least one microphone, and/or at least one clock 311, such as at least one clock crystal.

The communication device 300 can be implemented within the housing of the medicament delivery device, e.g. by at least partly exchanging the indicator assembly 180 at the distal end of the medicament delivery device 1 with the communication device covered by a semi-transparent lid/indicator 320, as is shown in FIG. 3b. In FIG. 3b, the position of the mechanical switch 301 in relation to an activation/click wall 313 before activation of the medicament delivery device is illustrated.

According to an embodiment, the at least one clock 311, such as e.g. a clock crystal device, which can be mounted on the PCB 302, can be configured to count a relative time related to the delivery of drugs. Thus, the at least one clock 311 can then count the elapsed period of time from the medicament delivery, such as from the start of the medicament delivery, i.e. from the point in time when the determination unit was activated. Hereby, the clock 311 may be in an off mode until the determination unit is activated, which saves battery power.

According to an embodiment, the transmission unit 304 is configured to create a connection between the communication device and the external receiving device, e.g. a smartphone, essentially directly at the activation of the communication device 300. The transmission unit 304 can also, as described in this document, be configured to transmit various information from the communication device 300 to the external receiving device. Hereby, interactive information may be presented by the smartphone during the medicament delivery.

FIGS. 4a-c illustrate how the at least one determination unit is activated. FIG. 4a illustrates that the mechanical switch 301 is in a non-compressed/inactive state before the medicament delivery has started. Thus, the at least one determination unit is here still inactive, and the electronics are in off-mode in order to save battery power.

FIG. 4b illustrates that the communication device is rotated with the at least one rotating physical part 50, 60, 182 of the medicament delivery device 1 when the medicament is delivered. According to an embodiment of the present invention, the mechanical switch 301 is then rotated by this rotation, and is arranged in relation to at least one fixed activation wall 313 of the medicament delivery device 1 such that the mechanical switch 301 is pressed against the at least one activation wall 313 by the rotation. Thus, when the physical parts, such as e.g. the plunger driver 50, starts rotating, the mechanical switch 301 is also brought to rotation since the PCB rotates. Hereby, the mechanical switch 301 is compressed by the activation wall 313, and the switch is activated. The at least one activation unit is then configured to activate the at least one determination unit based on said detected rotation.

FIG. 4c illustrates an embodiment of the present invention, for which the at least one rotation detection arrangement includes at least one electromagnetic switch 321, such as e.g. a magnetic reed switch, configured to be activated by the rotation. Here, the at least one electromagnetic switch 321 is mounted on the rotating PCB 302 and is thus also rotated by the rotation. The electromagnetic switch 321 is arranged in relation to at least one magnet 322 being fixed on the medicament delivery device 1, e.g. on an activation wall 313, such that the electromagnetic switch 321 is activated when the electromagnetic switch 321 is brought to pass adjacent to the magnet 322 by the rotation, i.e. when the electromagnetic switch 321 is brought into the magnetic field of the magnet 322 by the rotation. In an electromagnetic switch as the one disclosed in this document enters a magnetic field, the magnetic field causes the electromagnetic switch to be activated.

Correspondingly to the mechanical switch 301, when the physical parts, such as e.g. the plunger driver 50, starts rotating, the electromagnetic switch 321 is also brought to rotation since it is attached to the rotating PCB. Hereby, the switch electromagnetic 321 is activated, whereby the rotation is detected. The at least one activation unit is configured to then activate the at least one determination unit based on the detected rotation.

According to an embodiment of the present invention, shown in FIGS. 5a-b, the at least one rotation detection arrangement includes at least one insulating strip 501 initially being positioned between two contact points 502, 503 before the rotation, such as between a first contact point 503 arranged directly on the PCB 302 and a second contact point 502 arranged on a connector, such as e.g. on a metal sheet, being forced/pressed against the first contact point 503. The at least one insulating strip 501 is here configured to be removed from between the two contact points 502, 503 by the rotation. The least one insulating strip 501 can be fixed on a non-rotating part of the medicament delivery device 1, such as for example on at least one activation/click wall 313. Thus, in the initial non-activated state of the medicament delivery device, the at least one insulating strip 501 is positioned between two contact points 502, 503, as shown in FIG. 5a.

As described above, the rotation of at least one physical part 50, 60, 182 caused by the activation of the medicament delivery device rotates the PCB 302, whereby the two contact points 502, 503 are withdrawn from the location on the medicament delivery device, e.g. the activation wall 313, where the at least one insulating strip 501 is fixed. Thus, by the rotation, a short circuit is created between the two contact points 502, 503 when the at least one insulating strip 501 is removed from between the two contact points 502, 503 by the rotation. This is illustrated in FIG. 5b, where a short circuit is created between the first and second contact points 502, 503.

Figure 6B:
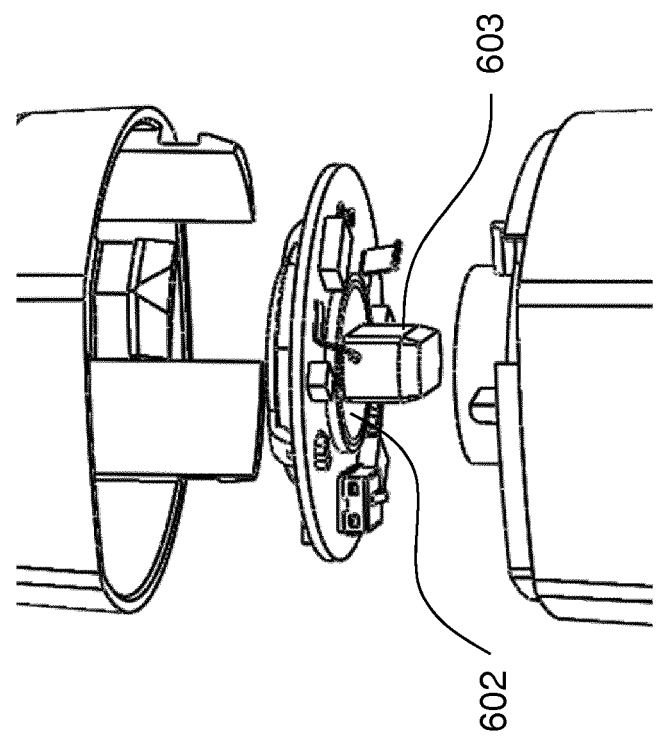
FIGS. 6a-d show parts of a communication device according to some embodiments.
Figure 6A:
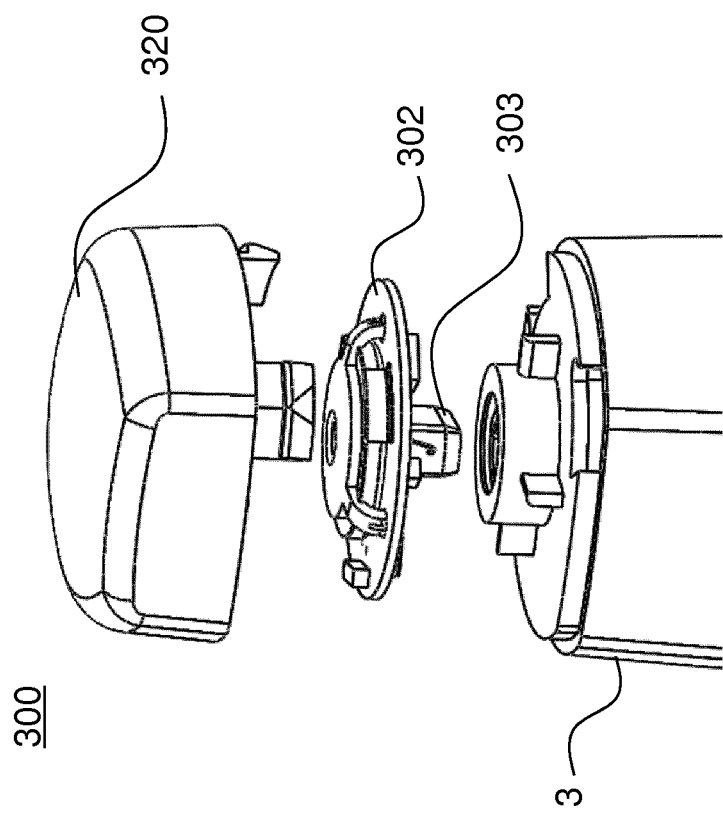
Figure 6D:
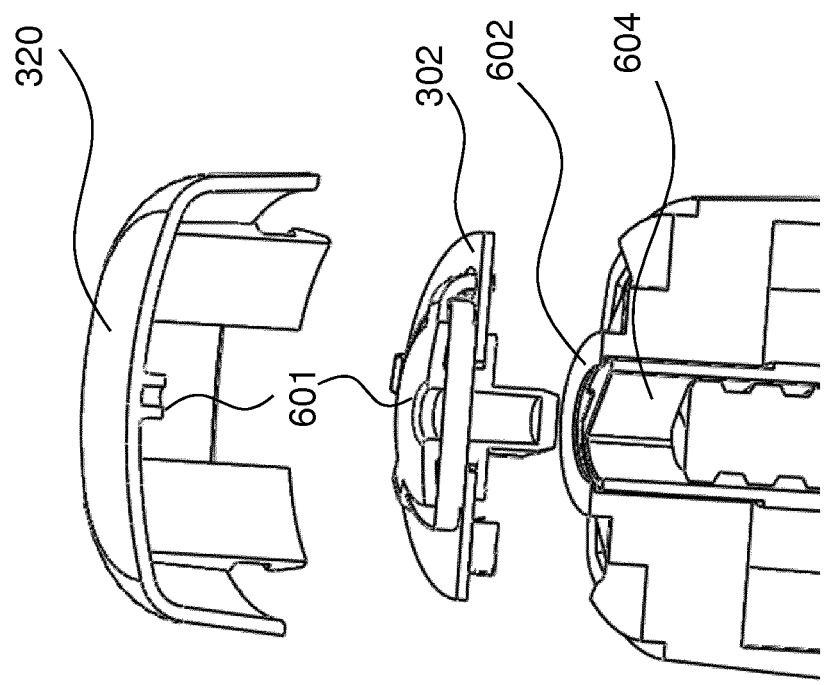
Figure 6C:
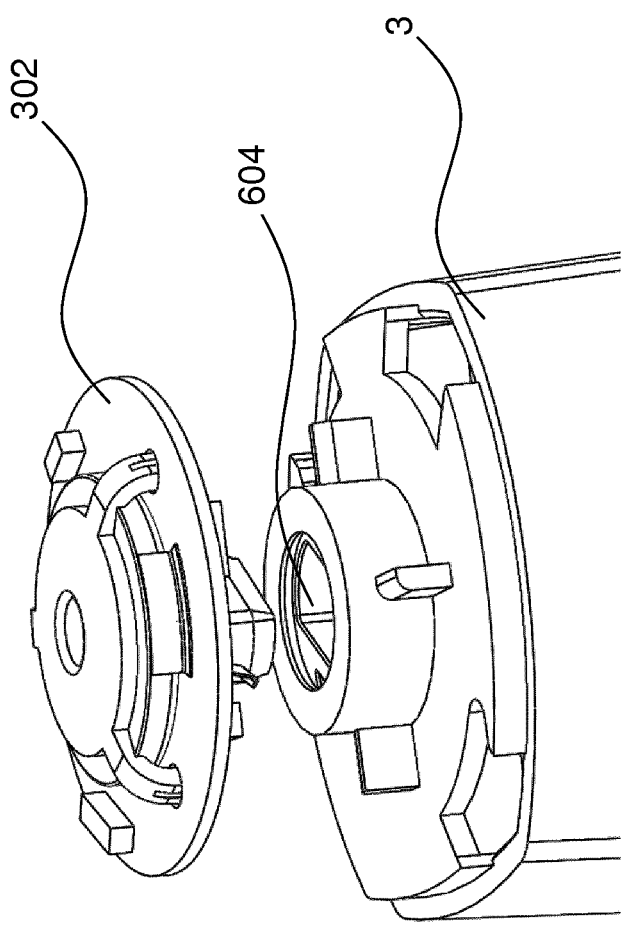

FIGS. 6a-d illustrate some parts of a communication device 300 having a rotatable PCB 302. As is shown in FIG. 6a-d, the communication device 300 can be arranged at a distal end of the housing 3 of the medicament delivery device 1, where the indicator assembly 180 is normally positioned. The communication device 300 includes at least one rotary shaft surface 603 on a driver/shaft 303. The rotary shaft surface 603 is connected to at least one corresponding rotary drive surface 604 of the medicament delivery device 1, such as e.g. a rotary drive surface 604 of the plunger driver 50. For example, the at least one rotary shaft surface 603 of the communication device 300 can be a male surface 603 and the corresponding at least one rotary drive surface 604 of the medicament delivery device 1 can be a female surface. Thus, when the at least one physical part 50, 60, 182 of the medicament delivery device rotates, the corresponding at least one rotary drive surface 604 of the medicament delivery device 1 rotates, which causes the at least one rotary shaft surface 603 of the communication device 300 to rotate, whereby also the PCB 302 rotates. As is shown in FIGS. 6*b-d*, the communication device 300 can include at least one axial contact/glide surface 602 between the housing 3 and the PCB 302. Also, at least one radial contact/glide surface 601 can be arranged between the rotatable PCD 302 and the lid 320. These contact/glide surfaces facilitate stable and low-frictional rotation of the PCB 302.

Figure 7C:
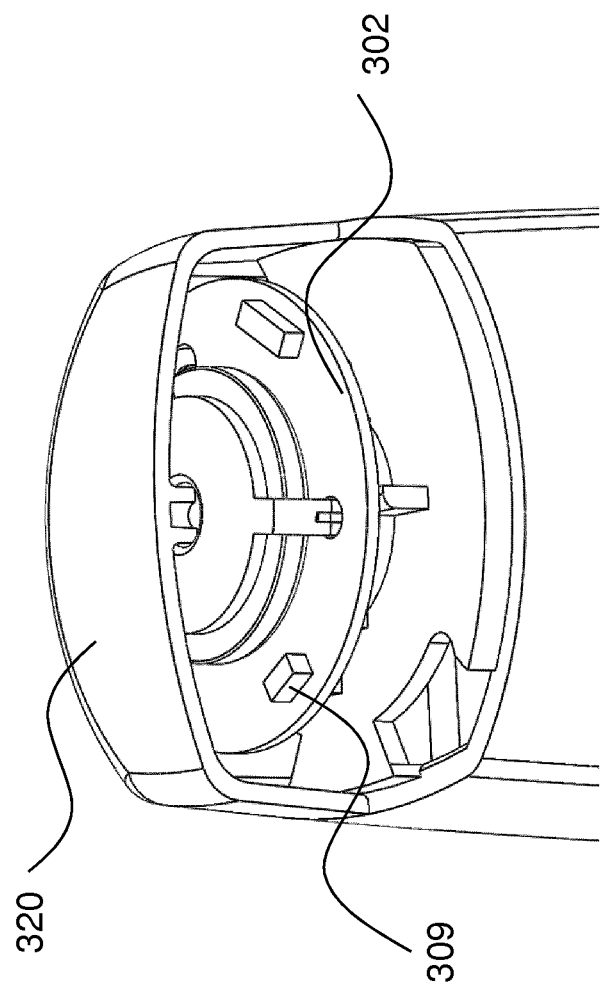

According to some embodiments of the present invention, shown in FIGS. 7*a-c*, the communication device 1 includes at least one indication unit 701, 702, 309 configured to provide at least one indication of that the medicament delivery is performed. The at least one indication can include visual, audible and/or tactile indications.

FIG. 7*a* shows an indication unit according to an embodiment creating audible and/or tactile indications, such as "click" sounds/vibrations. Here, a mechanical indication unit/source 701, is arranged on the rotatable PCB 302 and is configured to be compressed against a fixed part, such as e.g. a click wall 313, of the medicament delivery device by the rotation. The compression is followed by a subsequent release after further rotation. Hereby, clicking sounds and/or vibrations are created when the PCB 302, and therefore also the mechanical indication source 701, rotates, which can be used as indications to the user that the medicament delivery is in progress. For this embodiment, the mechanical indication source 701 can be implemented as the above described mechanical switch 301.

FIG. 7*b* shows an indication unit according to an embodiment creating more intense mechanical audible and/or tactile indications, such as louder "click" sounds and/or greater vibrations. According to this embodiment, one or more metal sheet parts 702 can be fixed to the rotatable PCB 302, e.g. by soldering and/or gluing. The one or more sheet metal parts 702 can then be configured to create a louder clicking and/or greater vibrations when the one or more sheet metal parts 702 are compressed against a fixed part, such as e.g. a click wall 313, of the medicament delivery devices by the rotation, and later released.

FIG. 7*c* shows an indication unit according to an embodiment creating a visual indication. Here, at least one light source, such as a Light Emitting Diode (LED) 309 is included in the indication unit. For example, the at least one LED can be arranged on the rotating PCB 302, or can be attached to another of the rotating parts of the communication device 300. During rotation, i.e. after activation of the at least one determination unit, the at least one LED 309 lights up. This rotating light is visible for a user through the lid 320, which may be semi-transparent or transparent, and/or can include a light guide, and can be used as a distinct indication for that the medicament delivery is in progress.

According to an embodiment of the present invention, the at least one indication being provided during the medicament delivery, e.g. the above described visual, audible and/or tactile indications exemplified in FIGS. 7*a-c*, can also be provided during a predetermined time period after the delivery has ended. This is possible since the communication device according to the present invention is provided with a source of energy, such as a battery, which can be used for providing this indication, e.g. letting a LED 309 shine, also after the medicament has been delivered. When the medicament delivery device 1 is pressed against the skin of the patient both during the delivery time, i.e. during the rotation/delivery, and also during the predetermined time period after the rotation/delivery, the medicament being delivered by the medicament delivery device 1 has enough time to be absorbed by the tissue of the patient. Thus, the predetermined time period can here be set, e.g. depending on the type of drug being delivered, such that the drug is sufficiently absorbed during the rotation/delivery and the predetermined time period.

According to an embodiment of the present invention, the at least one rotation detection arrangement of the communication device 300 includes at least one vibration sensor 312 (shown in FIG. 3*a*), such as e.g. at least one microphone. The at least one vibration sensor 312 is configured to pick up a predetermined vibration profile corresponding to a vibration profile being created by the medicament delivery device 1 by the rotation. For example, a microphone 312 can be mounted on the PCB 302 in order to pick up sounds and/or vibrations, such as the above described clicking sounds, being created by the at least one indication unit 701, 702.

Figure 8C:
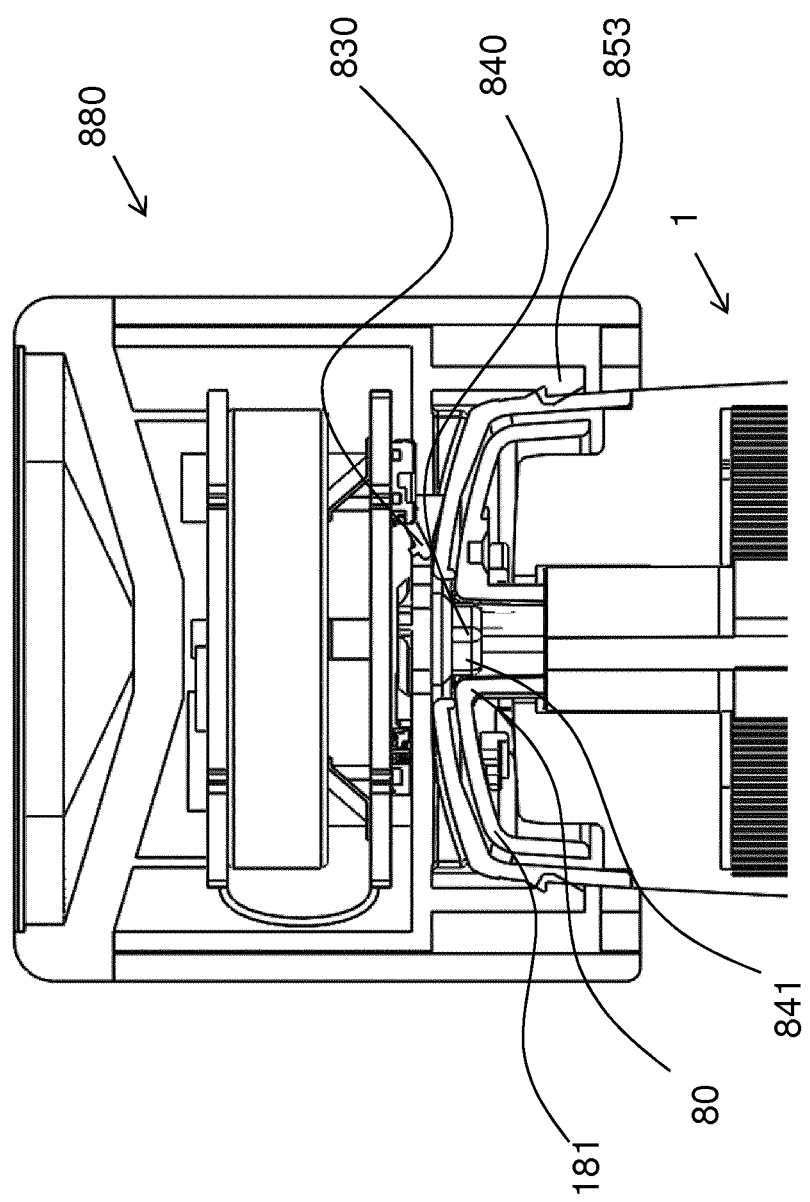

According to an embodiment of the present invention, the communication device 800 is included in an external unit 880, as shown in FIGS. 8*a-c*, possibly included within a lid 820, a housing 851 and/or a cover 852, which is releasably attachable to the medicament delivery device 1. Essentially any releasable attachment to the medicament delivery device providing a solid attachment can here be used, such as e.g. flexible snap fits 853 being included in the housing 581.

According to an embodiment, the housing 851 can be mechanically keyed to a specific medicament delivery device. The housing 851 may then be provided with a specific surface, including e.g. recesses/cavities/notches 855 corresponding to a surface pattern, e.g. including protrusions 856 (see FIGS. 9*a* and 10*c*) such as bars of a specific width and/or form, of a lid or a signaling element 182 of a medicament delivery device 1. Thus, the communication device 800 can here only be attached to the medicament delivery device 1 if the surface patterns of the housing 851 fits into the surface pattern of the lid or an signaling element 182 of a medicament delivery device 1. Hereby, each communication device 800 may be mechanically keyed to a specific medicament delivery device 1. Also, since the two surface patterns then fit together when the communication device 800 is attached to the medicament delivery device, a more solid attachment is achieved.

FIG. 8*a* shows an exploded view of a number of parts that can be included in a communication device 800 according to different embodiments of the present invention. According to an embodiment, the communication device itself is configured to be mainly fixed, except for a rotator 840 being configured to rotate with the rotation of the at least one physical part 50, 60, 182 of the medicament delivery device 1.

The communication device 800 illustrated in FIG. 8*a* includes at least one fixed PCB 802, and a transmission unit 804, such as e.g. a Bluetooth transmission unit, and an antenna unit 805 arranged on the at least one PCB 802 in order to transmit the information to the external receiver. The electronic circuits of the communication device 800 are provided with electrical power by a battery 806, such as a coin cell battery, via a battery connector 808. The communication device 800 can also, according to some embodiments, include at least one light source, such as a LED 809, and/or at least one clock 811, such as at least one clock crystal. The communication device 800 can also include at least one vibration sensor 812, such as e.g. at least one microphone.

According to an embodiment, the at least one clock 811, such as e.g. a clock crystal device, which can be mounted on the at least one PCB 802, can be configured to count a relative time related to the delivery of drugs. Thus, the at least one clock 811 can then count the elapsed period of time from the medicament delivery and/or from activation of the communication device 800. Hereby, the clock 811 may be in an off mode until the at least one determination unit is activated, which saves battery power.

According to an embodiment, the communication device 800 includes a transmission unit 804 being configured to creating a connection between the communication device and the external receiving device when the at least one determination unit is activated. The transmission unit 804 is also configured to transmit various information from the communication device 800 to the external receiving device. Hereby, interactive information may be presented e.g. by a smartphone during the medicament delivery. As stated above for transmission unit 304, essentially any suitable transmission format can be used for the transmission.

According to an embodiment, the communication device 800 includes an attachment switch 830, which is configured to be activated when the communication device is releasably attached to the medicament delivery device. Thus, the attachment switch is activated when the communication device 800 is mounted on the medicament delivery device 1, e.g. by mounting it on the distal end of the medicament delivery device 1 by pressing it against the distal end, thereby enabling activation of the communication device 800. Hereby, one or more parts of the communication device 300, such as e.g. the at least one rotation detection arrangement and/or the at least one transmission unit, may be activated by the attachment switch.

According to an embodiment, the communication device 800 includes a rotator 840 being configured to be rotated by the delivery rotation of at least one physical part 50, 60, 182 of the medicament delivery device 1, as is described below.

Figure 9C:
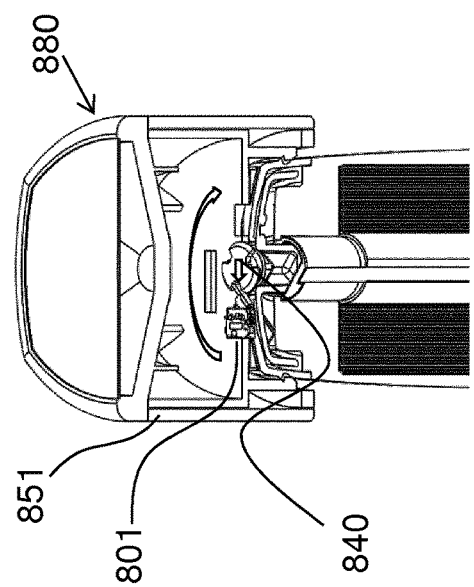
FIGS. 9a-c show parts of a communication device according to some embodiments.
Figure 9B:
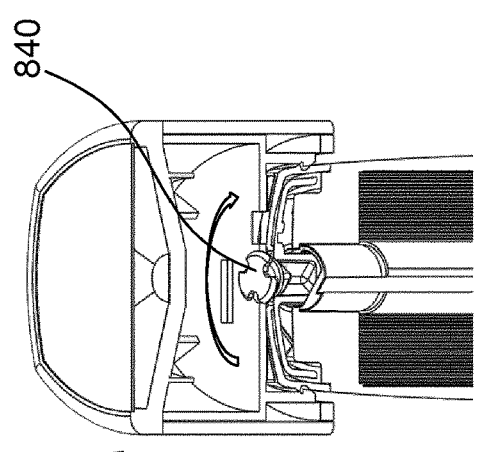
Figure 9A:
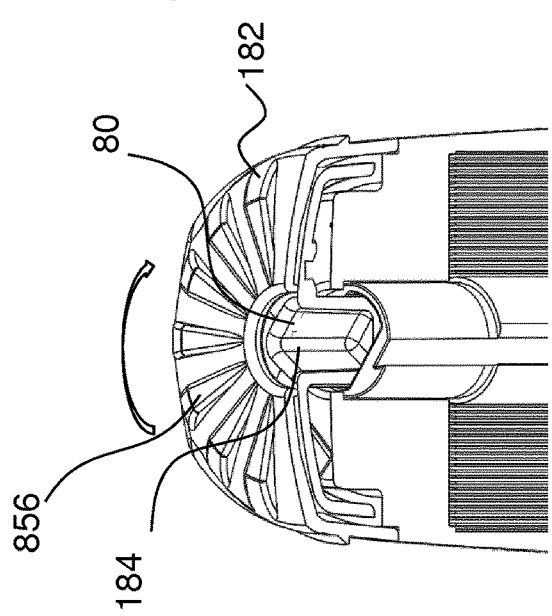

According to an embodiment of the present invention, the at least one rotation detection arrangement of the communication device 800 includes at least one mechanical switch 801, such as e.g. an injection switch, configured to be compressed by the rotation, and subsequently released. As is shown in FIGS. 9a-c, the mechanical switch 801 can be fixed, and arranged in relation the rotator 840 of the communication device 800 such that, when the rotator 840 is rotated by the rotation, the rotator 840 is pressed against the mechanical switch 801 by the rotation. For example, the mechanical switch 801 can be mounted/fixed on the housing 851 such that it is brought in contact with grooves on the rotator 840 when the rotator 840 rotates, thereby activating the mechanical switch 801.

According to an embodiment, the rotator 840 of the communication device 800 is connected to the indicator assembly 180, e.g. to the indicator 80, the indicator rod 82 and/or the signaling element 182 being part of the indicator assembly 180. The connection can be made e.g. by a squared shape design of a male part 841 of the rotator 840, fitting into a corresponding female squared shaped part 184 of the indicator assembly 180. Thus, when at least one part of the indicator assembly 180 rotates during the medicament delivery, the rotator 840 also rotates. Thereby, the at least one mechanical switch 801 is activated by the rotation. According to an embodiment, when both the attachment switch 830 and the mechanical switch/injection switch 801 are activated, the at least one determination unit is activated.

According to an embodiment shown in FIGS. 10a-d, the at least one rotation detection arrangement includes at least one electromagnetic switch 821, such as a reed switch, configured to be activated by the rotation of the at least one physical part of the medicament delivery device 1. This at least one electromagnetic switch 821 is here fixed, as it is attached to the fixed PCB 802. The at least one electromagnetic switch 821 is arranged in relation to at least one magnet 822 being configured to be rotated by the rotation. Hereby, the at least one electromagnetic switch 821 is activated when the at least one magnet 822 is brought adjacent to the at least one electromagnetic switch 821 by the rotation, i.e. when the at least one magnet 822 is brought so close to the at least one electromagnetic switch 821 that its magnetic field reaches the at least one electromagnetic switch 821 and thereby activates it.

FIGS. 10a-10d shows an exemplary implementation of this embodiment, in which the at least one magnet 822 is attached to the signaling element 182 of the indicator assembly 180 of the medicament delivery device 1. The signaling element 182 can here be in the form of a rotatable wheel or disk 182. When the signaling element 182 is rotated during the medicament delivery, the at least one magnet 822 is also rotated, as is illustrated in FIGS. 10c-d. A fixed electromagnetic switch 821 in the PCB 802 will hereby be passed by the at least one magnet 822 when it rotates, and will thus be activated.

According to an embodiment, the at least one magnet 822 can be attached on the inner and/or outer surface of the signaling element 182, and the communication device 800 is attached as an external unit 880 on the distal end of the medicament delivery device 1. Hereby, very few, or even no, changes would have to be done inside the actual medicament delivery device 1, which facilitates an implementation adding low costs and complexity to the device.

According to an embodiment, the at least one rotation detection arrangement of the communication device 800 includes at least one vibration sensor 812 (shown in FIG. 8a), such as e.g. at least one microphone. The at least one vibration sensor 812 is configured to pick up a predetermined vibration profile corresponding to a vibration profile being created by the medicament delivery device 1 by the rotation. For example, a microphone 812 can be mounted on the PCB 802 in order to pick up sounds and/or vibrations, such as the clicking sounds being created by the at least one mechanical switch 801 and/or being created by at least one indication unit of the communication device 800.

According to an embodiment of the present invention, at least one indication is provided during the medicament delivery, in form of e.g. visual, audible and/or tactile indications, as mentioned above. The indication unit is in FIG. 8a schematically illustrated by the LED 809 and a light guide 825. However, as is understood by a skilled person, also the above mentioned audible and/or tactile indications can be provided for the communication device 800 shown in FIG. 8a.

The indication unit can be configured to provide the indication during a predetermined time period after the delivery has ended. This is possible since the communication device 800 is provided with a source of energy, such as a battery 806, which can be used for providing this prolonged indication, e.g. by letting a LED 809 shine through the light guide 825, also after the medicament has been delivered. When the medicament delivery device 1 is pressed against the skin of the patient both during the delivery time, i.e. during the rotation/delivery, and during the predetermined time period after the rotation/delivery, the medicament being delivered by the medicament delivery device 1 has enough time to be absorbed by the tissue of the patient. As described above, the predetermined time period can be set, e.g. depending on the type of drug being delivered.

As mentioned above, the communication device 300, 800 described above can, according to an embodiment, include at least one determination unit configured to determine information related to a medicament delivery performed by the medicament delivery device. The information can be based on preconfigured data and/or measured data related to the medicament delivery. Such data may include e.g. an identification number identifying the medicament delivery device, an identification number identifying a medicament/drug being delivered by the medicament delivery device, an identification number identifying a patient using the medicament delivery device and/or an elapsed time since a delivery of a medicament/drug occurred.

According to an embodiment, the communication device 300, 800 described above can also be configured to determine information based on a number of revolutions of the at least one rotating physical part 50, 60, 182 of the medicament delivery device. The number of revolutions is here determined by the at least one rotation detection arrangement described above. The number of revolutions can then be included in the information transmitted to the external receiver from the communication device 300, 800.

The at least one determination unit is, according to an embodiment, also configured to compare the measured/determined number of revolutions with a correct number of revolutions being predetermined for the medicament delivery device 1. Alternatively, the external receiving device is configured to make the comparison, i.e. to compare the measured/determined number of revolutions with a correct number of revolutions being predetermined for the medicament delivery device 1. Normally, the correct number of revolutions needed for delivering the medicament to the patient is known, or can be calculated. Hereby, a problem occurring during the delivery and/or a malfunction of the communication device 800 can easily be detected simply by counting the number of revolutions actually being made for the delivery.

The present invention is not limited to the above described embodiments. Instead, the present invention relates to, and encompasses all different embodiments being included within the scope of the independent claims.

The invention claimed is:

1. A communication device arranged for transmitting information from a medicament delivery device comprising:
   a switch projecting proximally and configured to detect a rotation of at least one physical part of said medicament delivery device;
   a printed circuit board configured to determine information related to a medicament delivery performed by said medicament delivery device;
   a non-rotating wall positioned within the communication device or within a housing of the medicament delivery device and projecting distally so that the switch will engage the wall to activate the printed circuit board based on said detected rotation; and
   a transmitter that provides a wireless transmission of said information to an external receiving device,
   wherein the switch is rotated by the rotation relative to the wall such that a portion of the switch is pressed against the wall activating the printed circuit board.

2. The communication device as claimed in claim 1, wherein the switch comprises a mechanical switch configured to be compressed by said rotation.

3. The communication device as claimed in claim 1, wherein said printed circuit board is configured to determine said information based on at least one revolution of said at least one rotating physical part.

4. The communication device as claimed in claim 1, wherein said printed circuit board is configured to determine said information based on preconfigured data related to said medicament delivery, said data including one or more in the group of:
   an identification number for said medicament delivery device;
   an identification number for a medicament delivered by said medicament delivery device;
   an identification number for a patient using the medicament delivery device; and
   an elapsed time since a delivery of a medicament occurred.

5. The communication device as claimed in claim 1, wherein said printed circuit board is configured to determine said information based on measured data related to said medicament delivery, said data including one or more in the group of:
   an identification number for said medicament delivery device;
   an identification number for a medicament delivered by said medicament delivery device;
   an identification number for a patient using the medicament delivery device; and
   an elapsed time since a delivery of a medicament occurred.

6. The communication device as claimed in claim 1, wherein said communication device further includes at least one indication unit configured to provide at least one indication of that said medicament delivery is performed.

7. The communication device as claimed in claim 1, wherein said communication device further comprises at least one indication unit including one or more in the group of:
   at least one light source configured to emit light as said at least one indication;
   at least one light guide configured to guide light being emitted by at least one light source as said at least one indication;
   at least one mechanical audible indication source configured to be compressed and released by said rotation, thereby emitting the audible indication; and
   at least one mechanical tactile indication source configured to be compressed and released by said rotation, thereby providing the tactile indication.

8. The communication device as claimed in claim 1, wherein said communication device is included within a housing of said medicament delivery device.

9. The communication device as claimed in claim 1, wherein said communication device is included in an external unit, said external unit being releasably attachable to said medicament delivery device.

10. The communication device as claimed in claim 3, wherein said at least one revolution is measured by said at least one rotation detection arrangement.

11. The communication device as claimed in claim 6, wherein said at least one indication is provided during said delivery and also during a predetermined time period after said delivery has ended.

* * * * *